(12) United States Patent
Williams et al.

(10) Patent No.: US 10,980,440 B2
(45) Date of Patent: Apr. 20, 2021

(54) ELECTRODE DEVICE FOR MONITORING AND/OR STIMULATING ACTIVITY IN A SUBJECT

(71) Applicant: EPI-MINDER PTY LTD, East Melbourne (AU)

(72) Inventors: Christopher Edward Williams, East Melbourne (AU); Owen Burns, East Melbourne (AU)

(73) Assignee: EPI-MINDER PTY LTD, East Melbourne (AU)

(*) Notice: Subject to any disclaimer, the term of this patent is extended or adjusted under 35 U.S.C. 154(b) by 0 days.

(21) Appl. No.: 16/124,152

(22) Filed: Sep. 6, 2018

(65) Prior Publication Data
US 2019/0053730 A1  Feb. 21, 2019

Related U.S. Application Data

(63) Continuation of application No. PCT/AU2018/050048, filed on Jan. 25, 2018.

(30) Foreign Application Priority Data

Jan. 25, 2017  (AU) .............................. 2017900226

(51) Int. Cl.
  *A61B 5/00* (2006.01)
  *A61B 5/0478* (2006.01)
  (Continued)

(52) U.S. Cl.
  CPC .............. *A61B 5/0478* (2013.01); *A61B 5/04* (2013.01); *A61B 5/4094* (2013.01);
  (Continued)

(58) Field of Classification Search
  CPC ....... A61B 5/04; A61B 5/0416; A61B 5/0422; A61B 5/0478; A61B 5/6882;
  (Continued)

(56) References Cited

U.S. PATENT DOCUMENTS 4,328,813 A * 5/1982 Ray ...................... A61N 1/0539
                                                       607/139
4,350,161 A * 9/1982 Davis, Jr. .......... A61M 25/0023
                                                       251/339
(Continued)

FOREIGN PATENT DOCUMENTS

WO   WO-2016/049789 A2   4/2016

OTHER PUBLICATIONS

International Application No. PCT/AU2018/050048, International Search Report and Written Opinion, dated May 2, 2018.
(Continued)

*Primary Examiner* — Eun Hwa Kim
*Assistant Examiner* — Rachel A. Vierra
(74) *Attorney, Agent, or Firm* — Marshall, Gerstein & Borun LLP

(57) ABSTRACT

An electrode device is disclosed that is removably implantable at least partially in a bone or other tissue. The electrode device includes a head and a shaft connected to the head. The shaft has a shaft body extending distally from the head in an axial direction of the shaft, and a conductive element including a conductive surface at a distal end of the shaft. A plurality of discrete anchor elements can project from an outer surface of the shaft body in a transverse direction of the shaft. A conductive wire can be permanently fixed to a proximal end surface of the conductive element, the end surface being located in or adjacent the head. The head can have a convex outer surface and a concave inner surface. An electrode array and a reamer tool is also disclosed.

19 Claims, 7 Drawing Sheets

(51) Int. Cl.
*A61N 1/36* (2006.01)
*A61N 1/05* (2006.01)
*A61B 17/16* (2006.01)
*A61B 17/68* (2006.01)
*A61B 5/04* (2006.01)
*A61B 90/00* (2016.01)
*A61B 5/0416* (2006.01)

(52) U.S. Cl.
CPC .......... *A61B 5/6868* (2013.01); *A61B 17/162* (2013.01); *A61B 17/1695* (2013.01); *A61B 17/688* (2013.01); *A61N 1/05* (2013.01); *A61N 1/0526* (2013.01); *A61N 1/0529* (2013.01); *A61N 1/0539* (2013.01); *A61N 1/3606* (2013.01); *A61B 5/0416* (2013.01); *A61B 5/6864* (2013.01); *A61B 5/6882* (2013.01); *A61B 2090/036* (2016.02)

(58) Field of Classification Search
CPC ... A61B 5/6867; A61B 5/6868; A61B 5/6864; A61B 5/6878; A61B 5/686; A61B 5/6839; A61B 2562/0209; A61B 5/4094; A61B 17/132; A61B 17/1695; A61B 17/688; A61B 2090/036; A61N 1/0526; A61N 1/0551; A61N 1/05; A61N 1/0529; A61N 1/0539; A61N 1/3606
See application file for complete search history.

(56) References Cited

U.S. PATENT DOCUMENTS

| | | | | |
|---|---|---|---|---|
| 4,685,466 A | * | 8/1987 | Rau | A61B 5/04082 600/387 |
| 4,936,306 A | * | 6/1990 | Doty | A61B 5/0478 600/373 |
| 7,010,351 B2 | * | 3/2006 | Firlik | A61N 1/0531 607/2 |
| 8,068,892 B2 | | 11/2011 | Russell | |
| 8,116,875 B2 | | 2/2012 | Osypka et al. | |
| 2005/0075680 A1 | | 4/2005 | Lowry et al. | |
| 2005/0177039 A1 | | 8/2005 | Mills et al. | |
| 2007/0043372 A1 | * | 2/2007 | Willmann | A61B 17/863 606/264 |
| 2008/0033503 A1 | | 2/2008 | Fowler et al. | |
| 2009/0118804 A1 | | 5/2009 | Moffitt et al. | |
| 2018/0160929 A1 | * | 6/2018 | Ashe | A61B 5/0478 |
| 2018/0215941 A1 | * | 8/2018 | Hagar | C09D 11/03 |

OTHER PUBLICATIONS

Supplementary European Search Report issued in European Patent Application No. 18744071 dated Jun. 4, 2020.
McMorland et al., "Baseplate for two-stage cranial mounting of BMI connectors," *Journal of Neural Engineering*, vol. 10, No. 3 (2013).
Benovitski et al., "Ring and peg electrodes for minimally-Invasive and long-term sub-scalp EEG recordings," *Epilepsy Research, Elsevier Science Publishers*, vol. 135 (2017).
Barnett et al., "Epidural Peg Electrodes for the Presurgical Evaluation of Intractable Epilepsy," *Neurosurgery*, vol. 27, No. 1 (1990).
Awad et al., "A new class of electrodes of 'Intermediate Invasiveness': Preliminary experience with epidural pegs and foramen ovale electrodes in the mapping of seizure foci," *Neurological Research*, vol. 13, No. 3 (1991).
Lim et al., "Use of Intracranial Neurophysiologic Recording Techniques in the Evaluation for Epilepsy Surgery in Children," *Singapore Medical Journal*, (1992).

* cited by examiner

ELECTRODE DEVICE FOR MONITORING AND/OR STIMULATING ACTIVITY IN A SUBJECT

CROSS-REFERENCE TO RELATED APPLICATION

The present application claims priority to Australian provisional application no. 2017900226, filed on 25 Jan. 2017, the entire content of which is herein incorporated by reference.

TECHNICAL FIELD

The present disclosure relates to electrode devices to monitor and/or stimulate activity in a subject, including electrode devices for monitoring brain activity such as epileptic events, strokes or other events.

BACKGROUND

Epilepsy is considered the world's most common serious brain disorder, with an estimated 50 million sufferers worldwide and 2.4 million new cases occurring each year. Epilepsy is a condition of the brain characterized by epileptic seizures that vary from brief and barely detectable seizures to more conspicuous seizures in which a sufferer vigorously shakes. Epileptic seizures are unprovoked, recurrent and due to unexplained causes.

Ischemic stroke is also a very common medical condition in which cerebral blood flow (CBF) is compromised resulting in changes in brain function. If severe this leads to an infarct. Around the infarct is a penumbra region where function is depressed. Together these cause loss of function such as motor and sensory capability.

It is desirable to have a safe, reliable and/or comfortable means of monitoring brain activity, including, for example, to detect the occurrence of epileptic seizures, to enable monitoring of seizure frequency and severity with a view to diagnosing epilepsy and/or determining appropriate seizure control strategies and/or including, for example, to detect the onset of ischemic stroke. It is also desirable to have a safe, reliable and/or comfortable means of stimulating brain activity for providing therapy or otherwise.

Current techniques for monitoring brain activity such as epileptic seizures rely on EEG recordings, typically performed using EEG electrodes attached to the outer surface of the scalp or via surgically implanted intracranial EEG electrodes.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

In one aspect, the present disclosure provides an electrode device that is removably implantable at least partially in a bone or other tissue, the electrode device comprising:
a head; and
a shaft connected to the head; the shaft comprising:
a shaft body extending distally from the head in an axial direction of the shaft;
a conductive element, the conductive element including a conductive surface at a distal end of the shaft; and
a plurality of discrete anchor elements projecting from an outer surface of the shaft body in a transverse direction of the shaft.

The shaft of the electrode device may be configured for locating in a recess formed in a bone or other tissue. The recess may be a hole that is formed in the bone or tissue by drilling, cutting, reaming or otherwise. The anchor elements may distort on inserting of the shaft into the recess and assist with gripping between the shaft and surfaces defining the recess. The anchor elements may act substantially as one-way barbs, for example. The electrode device may be configured for insertion into the recess in the direction of the shaft axis, e.g. by press-fitting or plugging of the electrode device into the recess, for example. The electrode device may therefore have no screw thread, for example.

The anchor elements may be configured to distort significantly during removal of the electrode device from the recess. The anchor elements may be configured to remain intact (e.g. whole, unbroken and/or undamaged), during and after removal of the electrode device from the recess. The anchor elements may remain connected to the outer surface of the shaft body during and after removal of the electrode device from the recess. The anchor elements may substantially retain or substantially return to their original shape and configuration (their pre-implantation shape and configuration) after removal of the electrode device from the recess.

The shaft body may be formed of a first material and the anchor elements may be formed of a second material, the first and second materials having different properties. The second material may be softer than the first material. One or both of the first and second materials may be an elastomeric material. The elastomeric material may be silicone or another type of elastomeric material. In some embodiments, the first material may be a first elastomeric material and the second material may be a second elastomeric material, wherein the second elastomeric material has a lower durometer than the first elastomeric material.

The head may be formed of a third material. The third material may be the same as the second material. For example, the third material may also be an elastomeric material, e.g. a silicone material.

The anchor elements may be integrally formed, in one-piece, with the shaft body. Likewise, the shaft body may be integrally formed, in one-piece, with all or part of the head.

The anchor elements may be arranged in a staggered pattern on the outer surface of the shaft body. Thus, at least one anchor element of the plurality of anchor elements may be located, in the axial direction of the shaft, closer to the distal end of the shaft than one or more other anchor elements of the plurality of anchor elements. In some embodiments, a first pair of anchor elements of the plurality of anchor elements may be located, in the axial direction of the shaft, at a first distance from the distal end of the shaft and a second pair of anchor elements of the plurality of anchor elements may be located, in the axial direction of the shaft, at a second distance from the distal end of the shaft, the first and second distances being different. The anchor elements of the first pair may be located on opposite sides of the shaft body along a first transverse axis of the shaft and the anchor elements of the second pair may be located on opposite sides of the shaft body along a second transverse axis of the shaft, the first and second transverse axes being substantially orthogonal to each other. The staggered arrangement of anchor elements may reduce insertion forces required to insert the shaft of the electrode device into a recess.

In some embodiments, four anchor elements may be provided. However, in alternative embodiments, a variety of different numbers of anchor elements may be used.

Each anchor elements may have a wedge shape. The wedge shape may taper in thickness towards the distal end of the shaft. The wedge shape may be defined at least partially by a rear surface that faces the head of the device and a side surface that extends from an outer edge of the rear surface towards the distal end of the device. The rear surface may extends across a plane having an angle relative to a transverse plane of the device that is greater or equal to 5°, for example. The side surface may be curved.

The conductive element may extend at least partially along the shaft body in the axial direction. The shaft body may have a substantially cylindrical or a frustoconical outer shape. The shaft body may comprise an internal chamber in which the conductive element is at least partially located. The internal chamber may be defined by a wall of the shaft body. The inner surface of the wall may be cylindrical. The thickness of the wall may taper towards the distal end of the shaft. The internal chamber may have a distal end opening through which the conductive element extends. The conductive element may have a first portion located in the internal chamber, proximally of the distal end opening and a second portion located outside of the internal chamber, distally of the distal end opening. The first portion may be cylindrical, for example. The second portion may be dome-shaped and/or hemispherically shaped, for example.

The first portion of the conductive element may extend through the shaft body along at least 50%, or at least 60%, or at least 70%, or at least 80%, or at least 90%, or all of the axial dimension of the shaft body. The conductive element may be inserted into and/or encased by the shaft body during manufacture of the electrode device (e.g., as opposed to during use of the electrode device by a clinician). The conductive element may be inherently rigid and provide a stiffening core to the shaft body, which may enable easier insertion of the shaft into the recess, with relatively low compression of the shaft body. Across a transverse plane of the shaft, the conductive element may have a diameter that is greater than 50% of the diameter of the shaft body, greater than 60% of the diameter of the shaft body, or greater than 70% of the diameter of the shaft body.

The electrode device may comprise a conductive wire that is electrically connected to the conductive element. The conductive wire may extend through the head of the electrode device. The conductive element may have proximal end surface, wherein the conductive wire contacts and electrically connects to the proximal end surface. The conductive wire may be permanently fixed to the proximal end surface.

In one aspect, the present disclosure provides an electrode device that is removably implantable at least partially in a bone or other tissue, the electrode device comprising:
 a head; and
 a shaft connected to the head; the shaft comprising:
 a shaft body extending distally from the head in an axial direction of the shaft; and
 a conductive element extending through the shaft body in the axial direction, the conductive element including a conductive distal end surface and a conductive proximal end surface, the proximal end surface being located in or adjacent the head;

wherein a conductive wire is permanently fixed to the proximal end surface.

In any of the above aspects, by permanently fixing the conductive wire to the proximal end surface, the electrode device can be manufactured in a sealed arrangement, reducing possible electrical leakage or component damage. The conductive wire may be welded or soldered to the proximal end surface, for example. The proximal end surface of the conductive element may be located inside the head of the conductive device. The proximal end surface of the conductive element may comprise a recess in which the conductive wire contacts and electrically connects to the proximal end surface. The recess may be a channel and the channel may extend across an entire diameter of the proximal end surface. The recess may have one or more functions. For example, the recess may retain molten material during the welding or soldering. Moreover, material forming the head of the electrode device may extend into the recess, e.g. while in a fluid state during manufacture, helping to secure the conductive element in position and helping to protect the connection between the conductive wire and the conductive element.

The electrode device may further comprise a lead connected to the head of the electrode device and the conductive wire may also extend from the head of the device and through the lead. In alternative embodiments, the electrode device may comprise a port for connecting the conductive wire to a separate lead.

The lead may extend from the head at a strain relief portion of the head. The stain relief portion may be a portion of the head that tapers in width, across a transverse plane of electrode device, towards the lead. The strain relief portion may be curved to match a curvature of a skull. Across a transverse plane of electrode device, the head, including the strain relief portion, may have a tear-drop shape.

The lead may be integrally formed, in one-piece, with the head. The lead may therefore also be integrally formed, in one-piece, with the shaft body. The shaft body, head and lead may be permanently fixed together. The lead may include a fourth material that surrounds the conductive wire. The fourth material may be the same as the third material used in the head and/or the second material used in the shaft body. For example, the fourth material may also be an elastomeric material, e.g. a silicone material. Thus, a continuous body of elastomeric material may be provided in the electrode device that extends across the lead, the head and the shaft body. Following manufacture, none of these parts of the electrode device may need to be connected together by a user such as a surgeon. This may increase strength and cleanliness of the electrode device and may also improve ease of use.

The head of the electrode device may have a convex outer surface and may have a concave inner surface.

In one aspect, the present disclosure provides an electrode device that is removably implantable at least partially in a bone or other tissue, the electrode device comprising:
 a head having a convex outer surface and a concave inner surface; and
 a shaft connected to the head at the inner surface of the head, the shaft including a shaft body extending distally from the head in an axial direction of the shaft and a conductive element including a conductive distal end surface.

In any of the above aspects, the convex outer surface may face in a generally proximal direction and the concave inner surface may face in generally a distal direction. An outer portion of the head may extend radially outwardly of the shaft body to an outer edge of the head. The outer portion may curve distally as it extends towards the outer edge. The outer portion may be relatively thin and flexible. The outer portion may be resiliently flexible and may act as a spring to place a tension on anchor elements when the shaft of the electrode device is in the recess. The outer edge may include a rim portion, which rim portion may be substantially flat, e.g. by having a substantially flat distal-facing surface. The curved head arrangement may conform to curvature of tissue, e.g. the skull, at which the electrode device is located and may enable tissue layers to slide over its outer surface without significant adhesion. The rim portion of the head may seal around the recess in which the shaft is located. The seal may reduce electrical leakage through tissue and reduce tissue growing under the head. The flexible outer portion of the head may flex in a manner that enables the shaft to reach into recess to a range of depths.

In one aspect, the present disclosure provides a method of surgically implanting an electrode device, the electrode device having a head and a shaft connected to the head; the shaft comprising a shaft body extending distally from the head in an axial direction of the shaft and a conductive element, the conductive element including a conductive surface at a distal end of the shaft, the method comprising inserting the shaft into a recess of a cranium such that the shaft extends into but not through the cranium. The conductive surface of the shaft may be inserted into the recess to a location in the lower table of the cranium. The recess in the cranium may not be open to the dura mater.

In any of the aspects, the electrode device may be used to monitor brain activity, such as epileptic brain activity or ischemic stroke brain activity, and/or to stimulate brain activity for a variety of different purposes such as recovery from stroke or to treat chronic pain or suppress seizures.

In one aspect, the present disclosure provides an electrode array comprising at least one electrode device according to any one of the preceding aspects and a processing device connected to the at least one electrode device.

The at least one electrode device may comprise a plurality of the electrode devices. The at least one electrode device may comprise four electrode devices. The processing device may be an implantable processing device.

The electrode devices may be connected to the processing device via respective leads and/or a cable section. The leads and/or cable section may be flexible, such that the electrode devices can be implanted at desired spaced apart positions of bone or tissue, such as the cranium. For example, four electrode devices can be provided that are configured in two pairs for monitoring and/or stimulating electrical activity, e.g. for monitoring and/or stimulating electrical activity at right and left hemispheres of the brain, respectively.

The processing device and the at least one electrode device may be formed in the electrode array as a one-piece construct. The processing device and the at least one electrode device may be permanently fixed together. Following manufacture, no parts of the electrode array may need to be connected together by a user such as a surgeon. This may increase strength and cleanliness of the electrode array and may also improve ease of use.

The processing device may be implantable under skin tissue. The processing device may include any one of more of: an electrical amplifier, a battery, a transceiver, an analogue to digital converter, and a processor to process electrical signals received from or transmitted to the electrodes devices. The processing device my can include a memory to store signal processing data. The processing device may be similar to a processing device of a type commonly used with cochlear implants, although other configurations are possible. Data processed and stored by the processing device may be transmitted from the processing device wirelessly, or via a wire, to an external computing device for analysing the data.

In aspects above, electrode devices are described that are configured to locate in respective recesses in bone or other tissue. As indicated, the recess may be a hole that is formed in the bone or tissue by drilling, cutting, reaming or otherwise.

According to one aspect of the present disclosure, a reamer tool is provided comprising:

a handle extending along a longitudinal axis of the reamer tool, a reamer bit positioned adjacent a longitudinal end of the handle for reaming a location of bone or tissue, the reamer bit being fixed in relation to the handle such that rotation of the handle causes rotation of the reamer bit; and a foot, the foot being rotatable relative to the handle and the reamer bit, and configured to brace the reamer tool against bone or tissue at one or more locations surrounding the reaming location.

In addition to the bracing, the foot may also provide a depth stop for the reaming.

The foot may be freely rotatable relative to the handle and the reamer bit. The foot may be freely rotatable relative to the handle and the reamer bit by virtue of a plain bearing coupling. The plain bearing coupling may be between the foot and a locking nut of the reamer tool, the locking nut securing the reamer bit to the handle.

The foot may be non-movable or movable relative to the reamer bit along the longitudinal axis of the reamer tool. The foot may be rotatable relative to the handle and the reamer bit, and movable relative to the reamer bit along the longitudinal axis of the reamer tool, by virtue of a screw bearing coupling. The screw bearing coupling may be between the foot and a locking nut of the reamer tool, the locking nut securing the reamer bit to the handle.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

By way of example only, embodiments of the present disclosure are now described with reference to the Figures, in which:

FIG. 3 shows an enlarged view of the electrode device at area B of FIG. 1a;

FIG. 4 shows a cross-sectional view of the electrode device along line A-A of FIG. 1a.

10a to 10c illustrate, respectively, an exploded oblique view, a side view of a first state, and a side view of a second state, of a reaming device according to another embodiment of the present disclosure.

DESCRIPTION OF EMBODIMENTS

Embodiments of the present disclosure relate to the monitoring and/or stimulation of electrical activity in body tissue of a subject using an electrode device. For example, the electrode device may be used to monitor brain activity, such as epileptic brain activity, and/or stimulate brain activity for a variety of different purposes. For example, in one embodiment, the electrode device may be used to monitor and/or stimulate brain activity relating to stroke. It may also be used to treat chronic pain or suppress seizures.

Figure 1A:
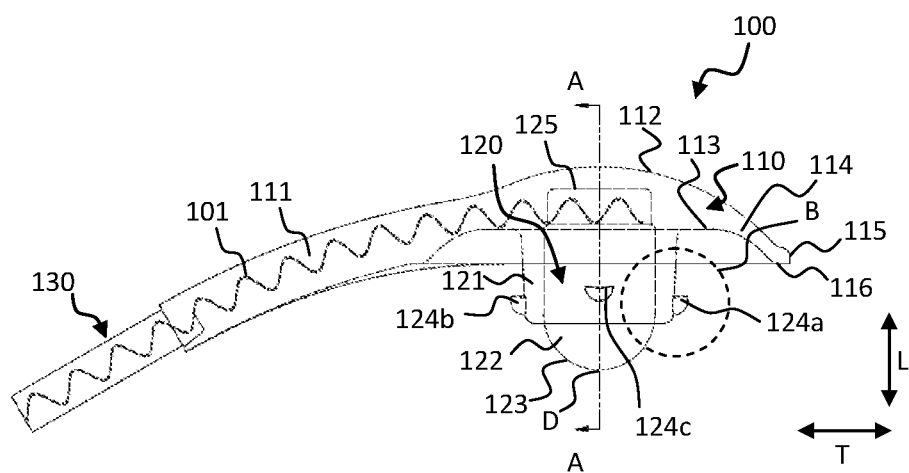
FIGS. 1a and 1b show side and top views, respectively, of an electrode device according to an embodiment of the present disclosure, in which internally located features of the electrode device are represented using broken lines.
Figure 1B:
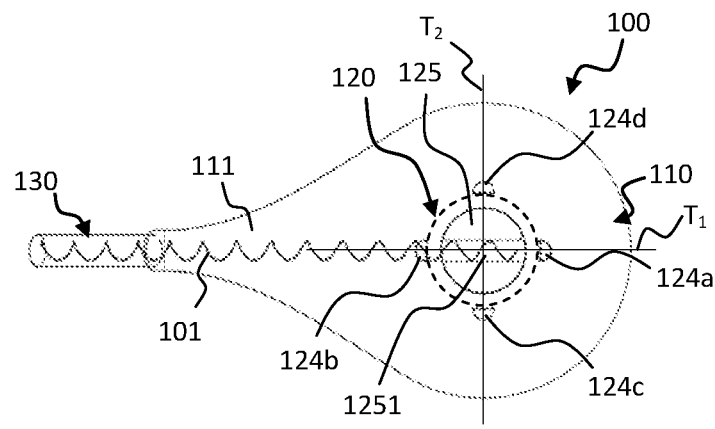
Figure 2:
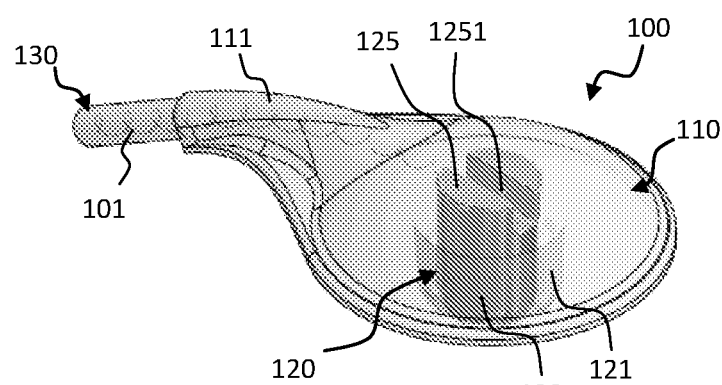
FIG. 2 shows a transparent oblique view of the electrode device of FIGS. 1a and 1b.

With reference to FIGS. 1a, 1b, and 2, in one embodiment an electrode device 100 is provided including a head 110 and a shaft 120, the shaft 120 being connected to the head 110. The shaft 120 includes a shaft body 121, a conductive element 122 and a plurality of discrete anchor elements 124a-124d. The shaft 120 extends distally from the head 110 in an axial direction L of the shaft 120. The conductive element 122 has a conductive surface 123 at a distal end D of the shaft 120. The elements 124a-d project from an outer surface of the shaft body 121 in a transverse direction T of the shaft that is perpendicular to the axial direction L. The electrode device 100 also includes a lead 130 to provide electrical connection to the electrode device 100. The electrode device includes a conductive wire 101 extending through the lead 130 and the head 110, the conductive wire 101 being electrically connected to the conductive element 122. In alternative embodiments, the electrode device may comprise a port for connecting to a separate lead.

Figure 5:
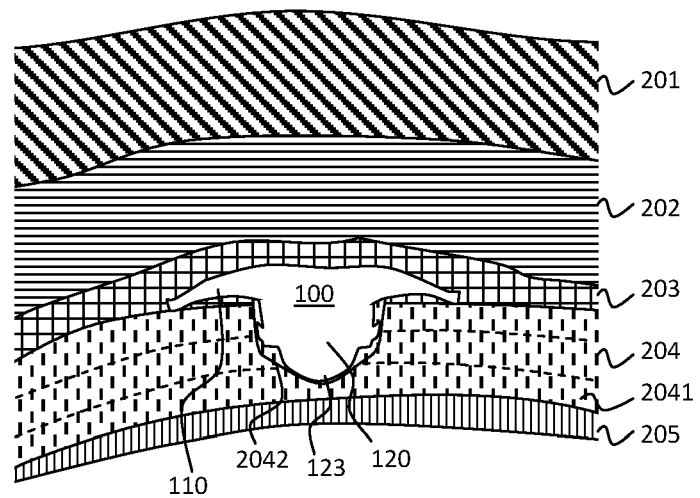
FIG. 5 shows a cross-sectional view of tissue layers of a scalp including a cranium in which a recess is formed to receive the electrode device of FIGS. 1a and 1b.

With reference to FIG. 5, the electrode device 100 of the present embodiment is configured to be at least partially implanted at a cranium 204 of a subject, and specifically such the shaft 120 projects into a recess 2042 formed in the cranium 204. The recess 2042 can be a burr hole, for example, which may be drilled and/or reamed into the cranium 204, e.g., to the depth of the lower table, without being exposed to the dura mater 205. FIG. 5 illustrates the positioning of the device 100 relative to various tissue layers adjacent to the cranium 204. The tissue layers illustrated include: skin 201; connective tissue 202; pericranium 203; cranium (bone) 204, including the lower table 2041 of the cranium 204; and the dura mater 205. As can be seen, substantially the entire axial dimension of the shaft 120 of the electrode device 100 extends into the recess 2042 while at least a rim at an outer edge of the head 110 abuts the outer surface of the cranium 204, in a pocket underneath the pericranium 203. The conductive surface 123 at the distal end D of the shaft 120 is positioned in the lower table 2041 of the cranium 204 such that it can receive electrical brain signals originating from the brain and/or apply electrical stimulation signals to the brain.

The electrode device 100 includes a number of features to assist in removably securing the shaft 120 at least partially in the recess 2042 in the cranium 204 (or a recess in any other bone or tissue structure where electrical monitoring and/or stimulation may be carried out). These features include, among other things, the anchor elements 124a-d. The anchor elements 124a-d are generally in the form of flexible and/or compressible lugs or barbs, which are configured to distort as the shaft 120 is inserted into the recess 2042 such that the anchor elements 124a-d press firmly against and grip the inner surfaces defining the recess 2042.

In this embodiment, referring to FIGS. 1a and 1b, the plurality of discrete anchor elements 124a-d include four spaced apart anchor elements 124a-d that are evenly distributed around a circumference of the outer surface of the shaft body 121 but which are in an offset or staggered arrangement in the axial direction L of the shaft body. Thus, some anchor elements 124a, 124b are located, in the axial direction L, closer to the distal end D of the shaft 120 than other anchor elements 124c, 124d. More specifically, in this embodiment, a first pair of the anchor elements 124a, 124b is located, in the axial direction L, at a first distance from the distal end D of the shaft, and a second pair of the anchor elements 124c, 124d is located, in the axial direction L, at a second distance from the distal end D of the shaft, the second distance being greater than the first distance. This arrangement of anchor elements 124a-d ensures that at least one of the pairs of anchor elements 124a-d is in contact with the inner surface of the recess 2042 and can allow for easier insertion of the shaft into the recess 2042. With reference to FIG. 1b, the anchor elements 124a, 124b of the first pair are located on opposite sides of the shaft body 121 along a first transverse axis $T_1$ of the shaft 120 and the anchor elements 124c, 124d of the second pair are located on opposite sides of the shaft body 121 along a second transverse axis $T_2$ of the shaft 120, the first and second transverse axes $T_1$, $T_2$ being substantially orthogonal to each other.

Figure 3:
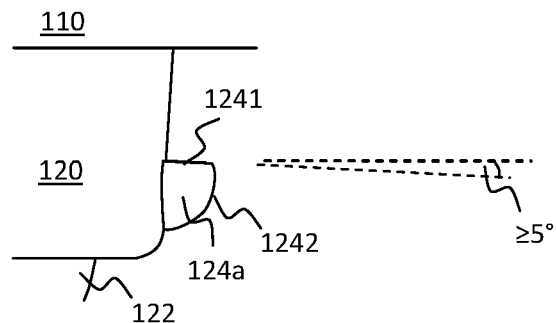

Referring to FIG. 3, which shows a close-up view of a portion of the electrode device 100 at area B of FIG. 1a, each anchor element 124a-d has a wedge shape. The wedge shape tapers in thickness towards the distal end D of the shaft 120. The wedge shape is defined by a rear surface 1241 that faces the head 110 of the device 100 and a curved side surface 1242 that extends from an outer edge of the rear surface 1241 towards the distal end D of the shaft 120. The rear surface 1241 extends across a plane having an angle relative to a transverse plane of the device that is greater or equal to 5°. This arrangement of the anchor elements 124a-d assists with gripping between the anchor elements 124a-d and the inner surface of the recess 2042.

Figure 4:
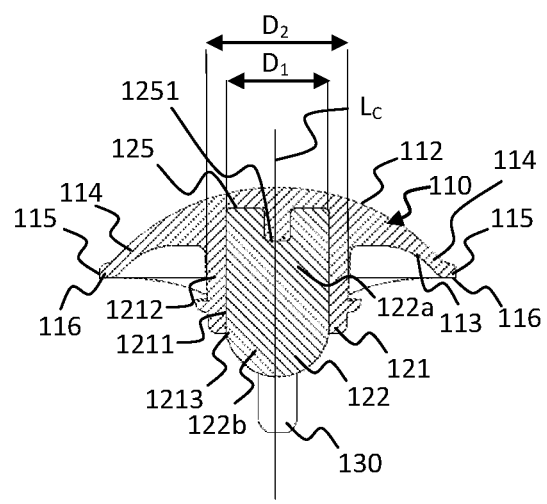

Referring to FIG. 4, which shows a cross-sectional view of the device 100 along line A-A of FIG. 1a, the shaft body 121 includes an internal chamber 1211 in which the conductive element 122 is partially located. The internal chamber 1211 is defined by an inner surface of a wall 1212 of the shaft body 121, the inner surface of the wall 1212 being cylindrical and coaxial with a central axis $L_C$ of the shaft 120 that extends in the axial direction L. The outer surface of the wall 1212 (which provides the outer surface of the shaft body 121) is angled relatively to the central axis $L_C$. In this embodiment, the outer surface is angled at about 2.7° relative to the central axis $L_C$. Thus, the thickness of the wall 1212 tapers towards the distal end D of the shaft 120. The shaft body 121 therefore has a substantially frustoconical outer shape. The frustoconical shape of the shaft body 121 aids insertion of the shaft 120 into the recess 2042 and provides for a progressively firmer grip between the shaft 120 and inner surfaces of the recess 2042, as the shaft 120 is inserted into the recess 2042.

The internal chamber 1211 has a distal end opening 1213 through which the conductive element 122 extends. The conductive element 122 has a first portion 122a located in the chamber 1211, proximally of the distal end opening 1213 and a second portion 122b located outside of the chamber 1211, distally of the distal end opening 1213. The first portion 122a is cylindrical and second portion 122b is dome-shaped or, more specifically, hemispherically-shaped in this embodiment. The first portion 122a of the conductive element 122 extends along the axial dimension of the shaft body 121 and into the head 110. In a transverse plane of the shaft 120, the conductive element 122 has a diameter $D_1$ that is greater than 50% of the diameter $D_2$ of the shaft body 121 and specifically about 75% of the diameter $D_2$ of the shaft body 121 in this embodiment. The conductive element 122 is formed of a conductive metal, specifically platinum metal in this embodiment. The conductive element 122 is inherently rigid and therefore provides a stiffening core to the shaft body 121, ensuring that the shaft 120 retains a relatively uniform shape during use.

The shaft body 121 is formed of a first material, the first material being an elastomeric material and more specifically a first silicone material in this embodiment. The anchor elements 124a-d are formed of a second material, the second material being an elastomeric material and more specifically a second silicone material in this embodiment. The first and second materials have different properties. In particular, the second material has a lower durometer than the first material. Accordingly, the second material is softer than the first material and thus the anchor elements 124a-d are formed of softer material than the shaft body 121. By forming the shaft body 121 of a relatively hard elastomeric material, the shaft body can be flexible and compressible, yet still substantially retain its shape on insertion into the recess 2042 in the bone. The stiffening core provided by the conductive element 122 also assists in this regard. On the other hand, by forming the anchor elements 124a-d of a relatively soft elastomeric material, the anchor elements are more flexible and compressible, which can allow easier removal of the shaft 120 from the recess 2042 after use of the electrode device 100. Indeed, the soft material may be provided such that anchor elements 124a-d distort significantly upon removal of the shaft 120 from the recess 2042.

The anchor elements 124a-d are configured to remain intact during removal of the shaft 120 from the recess 2042. Thus, no part of the electrode device may be left behind in the body after removal. The anchor elements 124a-d remain connected to the outer surface of the shaft body 121 during and after removal. Further, the anchor elements substantially retain their original shape and configuration after removal of the electrode device from the recess 2042.

As evident from FIG. 4, despite being formed of material having different properties, the anchor elements 124a-d are integrally formed, in one-piece, with the shaft body 121. Moreover, the shaft body 121 is integrally formed, in one-piece, with the head 110.

As discussed above, the electrode device includes a lead 130 that is connected to the head 110 of the electrode device 100, a conductive wire 101 extending through the lead 130 and the head 110, and electrically connecting to the conductive element 122. With reference to FIGS. 1a to 2, the conductive wire 101 is helically arranged such that it can extend and contract upon flexing of the electrode device including the lead 130 and the head 110. The conductive wire 101 contacts and electrically connects to a proximal end surface 125 of the conductive element 122. The conductive wire 101 is permanently fixed to the proximal end surface 125, e.g. by being welded or soldered to the proximal end surface 125. In this embodiment, the proximal end surface 125 of the conductive element 122 is located inside the head 110 of the conductive device 100. The proximal end surface 125 of the conductive element includes a recess 1251 in which the conductive wire 101 contacts and electrically connects to the proximal end surface 125. The recess 1251 is a channel in this embodiment, which extends across an entire diameter of the proximal end surface 125. The recess 1251 can retain molten material during the welding or soldering of the conductive wire 101 to the proximal end surface 125. Moreover, material forming the head 110 of the electrode device can extend into the channel, e.g. while in a fluid state during manufacture, helping to secure the conductive element 122 in position and helping to protect the connection between the conductive wire 101 and the conductive element 122.

In this embodiment, in addition to the shaft body 121 being integrally formed, in one-piece, with the head 110, the lead 130 is also integrally formed, in one-piece, with the head 110. A continuous body of elastomeric material is therefore provided in the electrode device 100, which continuous body of elastomeric material extends across the lead 130, the head 110 and the shaft body 120. The continuous body of elastomeric material covers the conductive wire 101 within the lead 130 and the head 110, covers the proximal end surface 125 of the conductive element 122 within the head 110 and surrounds sides of the conductive element 122 of the shaft 120. The arrangement is such that the lead 130, head 110 and shaft 120 are permanently fixed together and cannot be disconnected during normal use. Following manufacture, no parts of the electrode device 100 may need to be connected together by a user such as a surgeon. The one-piece nature of the electrode device 100 may increase strength and cleanliness of the electrode device 100 and may also improve ease of use.

Referring to FIGS. 1a to 2, the lead 130 is connected to the head 110 of the electrode device at a strain relief portion 111 of the head 110. The strain relief portion 111 is a tapered section of the head 110 that provides a relatively smooth transition from the head 110 to the lead 130. Specifically, the stain relief portion 111 is a portion of the head 110 that tapers in width, generally across a transverse plane of electrode device, to a connection with the lead 13. As evident from FIG. 1b, the head 110, including the strain relief portion 111, has a tear-drop shape.

The strain relief portion 111 is curved. The curvature is provided to match a curvature of the cranium 204 such that a reduced pressure, or no pressure, is applied by the strain relief portion 111 to the skull when the electrode device is implanted in position.

As can be seen in FIGS. 1a and 4, the head 110 has a convex outer (proximal-facing) surface 112 and a concave inner (distally-facing) surface 113. An outer portion 114 of the head 110 that extends radially outwardly of the shaft body 121, to an outer edge 115 of the head 110, curves distally as it extends towards the outer edge 115. Nevertheless, at the outer edge 115, the head 110 includes a flattened, rim portion 116 to provide a surface for atraumatic abutment and sealing with tissue. The outer portion 114 of the head 110 is resiliently flexible. Due to its resilient flexibility and curved shape, the outer portion 114 of the head 110 can act as a spring to place a tension on the anchor elements 124a-d when the shaft 120 is in the recess 2042. In general, the curved head arrangement may conform to curvature of tissue, e.g. the skull, at which the electrode device 100 is located and may enable tissue layers to slide over its outer surface 112 without significant adhesion. The rim portion 116 of the head 110 may seal around the recess 2042 in which the shaft 120 is located. The seal may reduce electrical leakage through tissue and reduce tissue growing under the head 100. The flexible outer portion 116 of the head 110 may also flex in a manner that enables the shaft 120 to reach into recess to a range of depths.

Figure 6A:
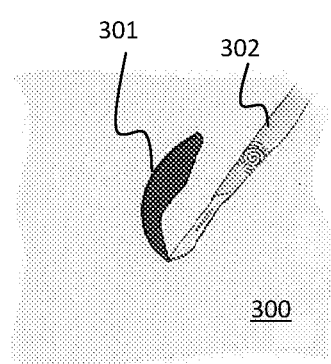
FIGS. 6a to 6f illustrate steps in a method of surgically implanting the electrode device of FIGS. 1a and 1b.
Figure 6B:
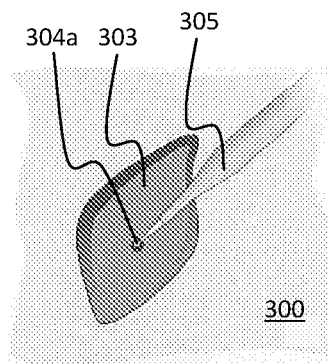
Figure 6C:
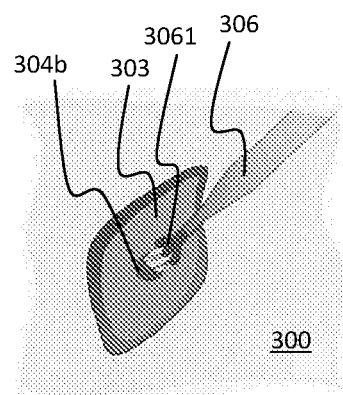
Figure 6D:
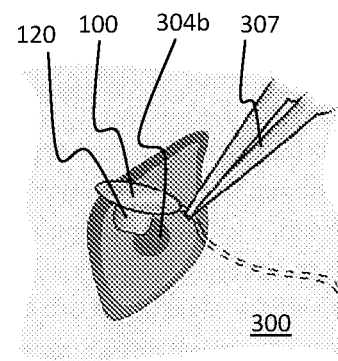
Figure 6E:
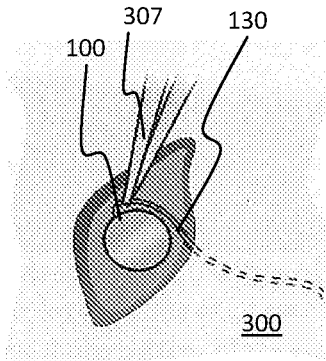
Figure 6F:
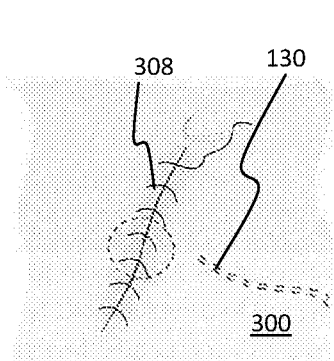

A method of surgically implanting the electrode device 100 is now described with reference to FIGS. 6a to 6f. At a scalp 300, an incision 301 is made using a scalpel 302 to form a flap of tissue, exposing the parietal bone 303 of the cranium (FIG. 6a). A hole 304a of a first diameter, e.g. a 3 mm diameter, is drilled into the parietal bone 303 to a depth of the lower table using a cutting burr 305 (FIG. 6b). The hole 304a is enlarged to become a hole 304b of a second diameter, e.g., a diameter of 4.5 mm, using a reamer tool 306 with a depth stop 3061 (FIG. 6c). The shaft 120 of the electrode 100 is inserted into the enlarged hole 304b using tweezers 307 (FIG. 6d). The conductive surface 123 of the shaft 120 is inserted into the hole 304b to a location in the lower table of the cranium, the hole 304b not being open to the dura mater. The electrode device 100 is rotated, after insertion of the shaft, about its axis using the tweezers 307, e.g. rotated by about 90 to 120 degrees, to take up slack in the lead 130 of the electrode device 100 (FIG. 6e). The scalp 300 is then closed, e.g. using sutures 308, in a layer-by-layer process (FIG. 6f). As indicated in FIG. 6f, the lead 130 can be routed underneath the outer surface of the scalp 300.

Figure 7:
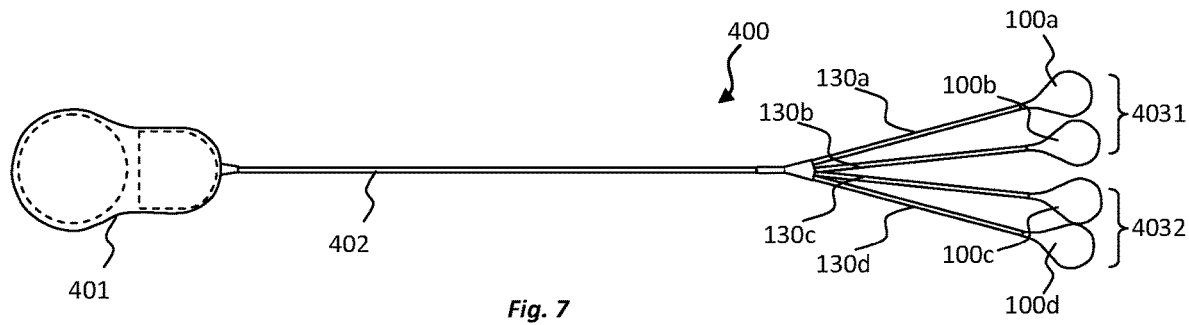
FIG. 7 shows a top view of an electrode array according to an embodiment of the present disclosure, the electrode array comprising a plurality of the electrode devices of FIGS. 1a and 1b.
Figure 8:
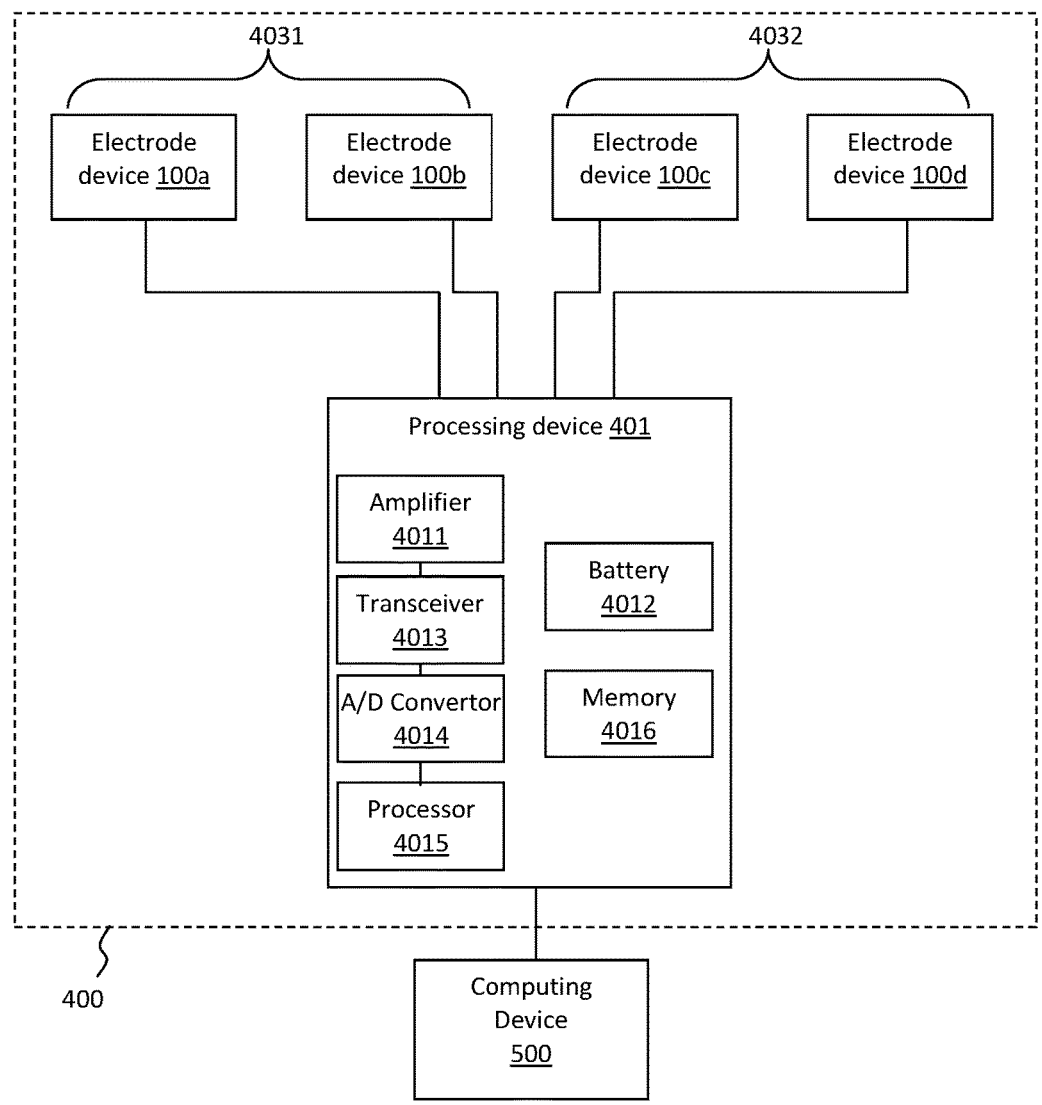
FIG. 8 is a schematic illustration of components of the electrode array of FIG. 7 in combination with a computing device.
Figure 9A:
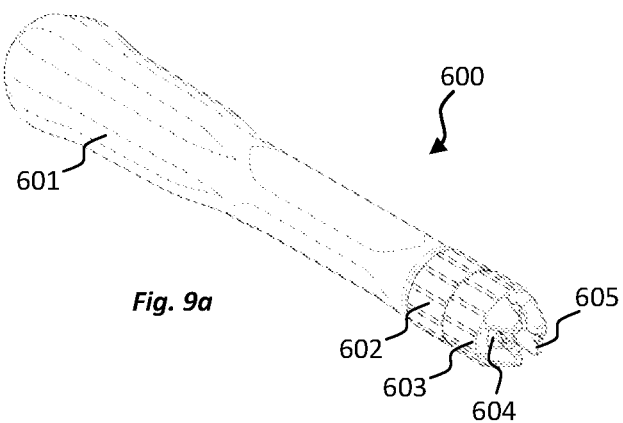
FIGS. 9a to 9d illustrate oblique, exploded oblique, side and end views, respectively, of a reaming device according to an embodiment of the present disclosure.
Figure 9B:
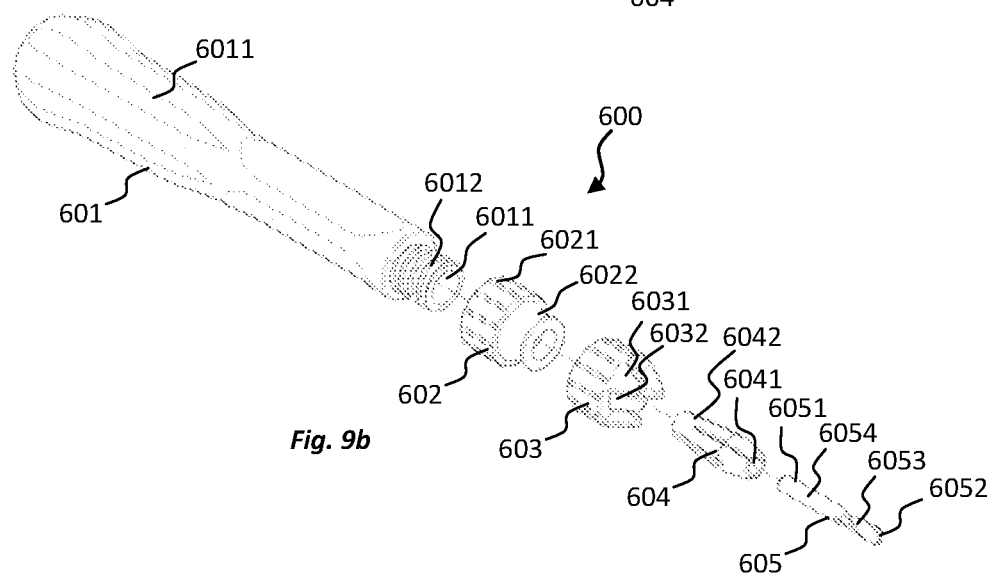
Figure 9C:
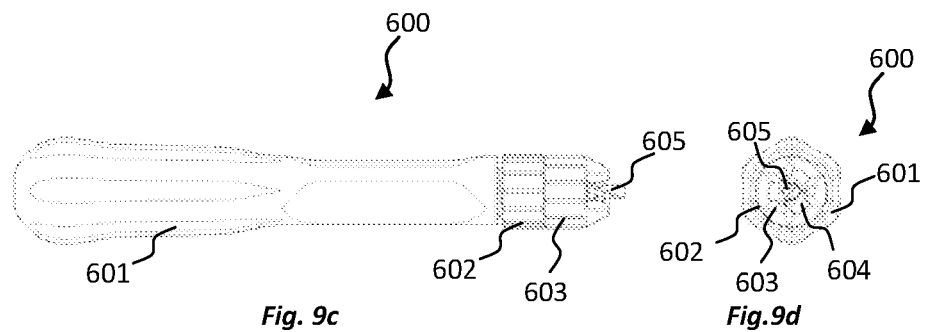
Figure 9D:
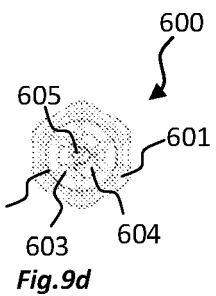

In one embodiment, as now discussed with reference to FIGS. 7 and 8, a plurality of the electrode devices 100 are provided in an electrode array 400. Specifically, in this embodiment, an electrode array 400 is provided that includes four of the electrode devices 100a, 100b, 100c, 100d that are connected via their respective leads 130a, 130b, 130c, 130d, and via a further cable section 402, to a processing device 401.

Due to the flexibility of the leads 130a-d and cable section 402, the four electrode devices 100a-d can be implanted at spaced apart positions of the cranium. The four electrode devices 100a-d can be configured in two pairs 4031, 4032 for monitoring and/or stimulating electrical activity, e.g. for monitoring and/or stimulating electrical activity at right and left hemispheres of the brain, respectively.

In this embodiment, the processing device 401 and electrode devices 100a-d (along with their respective leads 130a-d and the cable section 402) are formed in the electrode array 400 as a one-piece construct. The arrangement is such that the processing device 401 and the electrode devices 100a-d are permanently fixed together (for the purpose of normal operation and use). There is therefore no requirement or indeed possibility for a user, such as a surgeon, to connect these components of the electrode array 400 together prior to implantation, therefore increasing the strength, cleanliness and ease of use of the electrode array 400.

The processing device 401 may be implanted under skin tissue. With reference to FIG. 8, the processing device 401 can include an electrical amplifier 4011, a battery 4012, a transceiver 4013, an analogue to digital converter 4014, and a processor 4015 to process electrical signals received from or transmitted to the electrodes devices 100a-d. The processing device 401 can include a memory 4016 to store signal processing data. The processing device 401 may be similar to a processing device of a type commonly used with cochlear implants, although other configurations are possible.

The data processed and stored by the processing device 401 may be raw EEG data or partially processed (e.g. partially or fully compressed) EEG data, for example. The EEG data may be transmitted from the processing device 401 wirelessly, or via a wire, to an external computing device 500 for further processing and analysing of the data. The computing device 500 may analyse EEG signals to determine if a target event has occurred. Data regarding the event may be generated by the computing device 500 on the basis of the analysis. In one example, the computing device 500 may analyse brain activity signals to determine if a target event such as an epileptic event or stroke has occurred and data regarding the epileptic event or stroke may be generated by the computing device 500 on the basis of the analysis.

By carrying out data analysis externally to the electrode array 400, using the computing device 500, for example, there may be a reduction in power consumption within the electrode array 400, enabling the electrode array 400 to retain a smaller geometrical form. Moreover, the computing device 500 may have significantly higher processing power than would be possible with any processor included in the electrode array. The computing device 500 may run software that continuously records electrical data received from the electrode array 400.

The processing device 401 and/or computing device 500 can comprise a digital signal processor (DSP) and/or other components and/or software modules to carry out signal processing. In general, it will be recognised that any processer that is used may comprise a number of control or processing modules for controlling one or more features of the present disclosure and may also include one or more storage elements, for storing desired data, e.g., raw or processed EEG data. The modules and storage elements can be implemented using one or more processing devices and one or more data storage units, which modules and/or storage devices may be at one location or distributed across multiple locations and interconnected by one or more communication links. Computing devices 500 used in conjunction with the electrode array 400 may include microprocessors, desktop computers, laptop computers, tablets, smartphones, personal digital assistants and other types of devices, including devices manufactured specifically for the purpose of carrying out methods according to the present disclosure.

Further, the processing modules can be implemented by a computer program or program code comprising program instructions. The computer program instructions can include source code, object code, machine code or any other stored data that is operable to cause the processor to perform the steps described. The computer program can be written in any form of programming language, including compiled or interpreted languages and can be deployed in any form, including as a stand-alone program or as a module, component, subroutine or other unit suitable for use in a computing environment. The data storage device(s) may include suitable computer readable media such as volatile (e.g., RAM) and/or non-volatile (e.g., ROM, disk) memory or otherwise.

As discussed above with reference to FIGS. 6b and 6c, a reamer tool can be used in the process of forming a recess in bone (or other) tissue. A reamer tool 600 according to one embodiment of the present disclosure is now described with reference to FIGS. 9a to 9d. The reamer tool includes a handle 601, a lock nut 602, a foot 603, a collet 604 and a reamer bit 605.

The reamer bit 605 has a proximal end 6051 and a distal end 6052. A peripheral cutting edge 6053 for cutting bone or other tissue extends around the reamer bit 605 at a region adjacent the distal end 6052 of the reamer bit 605. The distal end 6052 of the reamer bit 605 is relatively flat in this embodiment, reducing the risk that it will cause unnecessary damage to bone or tissue. A shaft 6054 is provided adjacent the proximal end 6051 of the reamer bit 605. The shaft 6054 is received in a distal end opening 6041 of the collet 604. A tapered proximal end region 6042 of the collet 604 is seated in a tapered distal end opening 6011 of the handle 601 and is clamped in place in the handle opening 6011 by the lock nut 602. To achieve the clamping, the lock nut 602 surrounds the proximal end 6042 of the collet 604 and couples to the distal end opening 6011 of the handle 601 via engagement with surrounding screw threads 6012 of the handle 601. A proximal outer surface of the lock nut 602 includes knurling 6021 for gripping by a user when effecting the screw thread engagement between the lock nut 602 and the handle 601 and/or for gripping when holding the reamer tool 600 while carrying out a reaming step. The arrangement of the components of the reamer tool 600 is such that turning of the handle 601 will cause turning of the reamer bit 605 (and the other components 602, 604 that are directly or indirectly fixed thereto).

The foot 603 of the reamer tool is, however, rotatable relate to the handle 601, the reamer bit 605, and the other components 602, 604 of the reamer tool 600. The foot 603 can brace firmly against, and remain stationary relative to, the bone or other tissue during reaming. This provides for stabilization of the reamer tool 600 against the bone or other tissue, without causing bruising or damage to surrounding tissue. The foot 603 can also provide a depth stop for the reaming. In this embodiment, the foot 603 is freely rotatable relative to the other components of the reamer tool 600 by virtue of a plain bearing coupling and particularly a rotatable coupling of a smooth proximal inner surface 6032 of the foot 603 and a smooth distal outer surface 6022 of the lock nut 602.

The foot 603 is configured to contact the bone or other tissue at points that surround the region that is reamed. The foot 603 is a multi-legged foot and specifically, in this embodiment, a three-legged foot including three legs 6031 that are to makes contact with the bone or other tissue. The legs 6031 are spaced apart, allowing for visualization of the reamer bit 605 between the legs 6031.

In this embodiment, when the various components of the reamer tool 600 are assembled, the reamer bit 6052 projects from the foot 603 (see FIG. 9c) by a distance corresponding to the desired depth of the reamed hole. Accordingly, the foot 603 will only brace against the bone or other tissue surrounding the reamed hole when the reamer bit is at or very close to the full ream depth. At this depth, the foot 603 provides a depth stop.

Figure 10A:
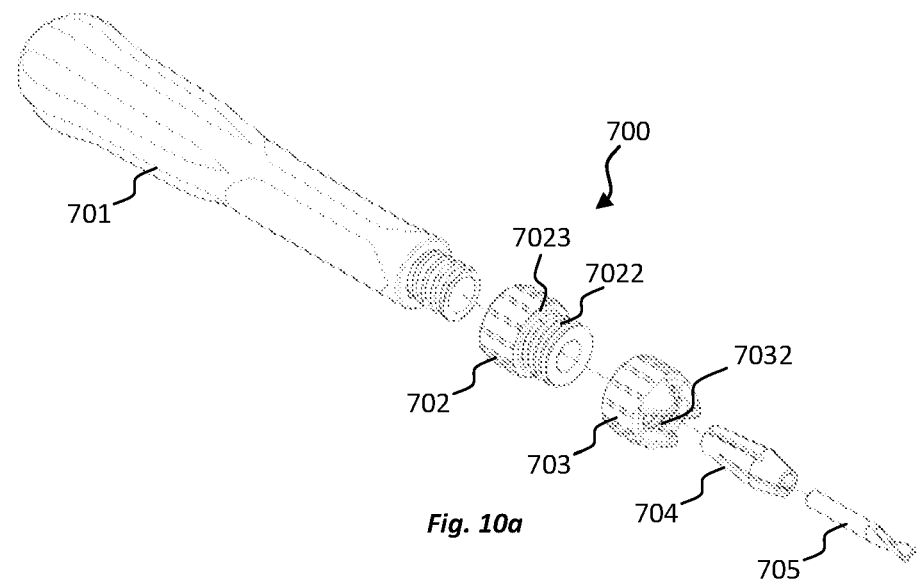
Figure 10B:
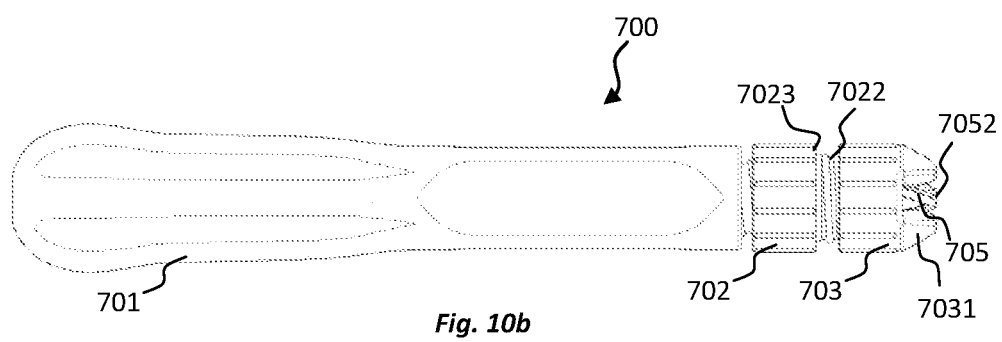
Figure 10C:
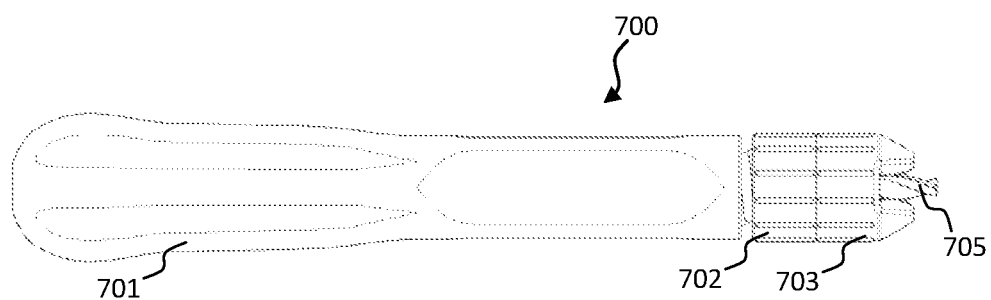

In alternative embodiments, the foot may be configured to brace against the bone or other tissue at different ream depths or all ream depths of the reamer bit. For example, in one embodiment of the present disclosure, now described with reference to FIGS. 10a to 10c, a reamer tool 700 is provided, including a handle 701, a lock nut 702, a foot 703, a collet 704 and a reamer bit 705, that is substantially identical to the reamer tool 600 described above, except for the rotatable coupling between the foot 703 and the lock nut 702. In this embodiment, rather than having a plain bearing coupling provided between smooth surfaces of the foot 703 and lock nut 702, which allows for free rotation of these parts, a screw bearing coupling is provided. The screw bearing is achieved by engagement between complimentary screw threads 7032, 7022 of the foot 703 and the lock nut 702. The screw bearing is such that the foot 703 can initially be positioned, on the screw bearing, towards a distal end of the lock nut 702. In this initial position, as illustrated in FIG. 10b, the ends of the legs 7032 of the foot 703 are substantially flush with the distal end 7052 of the reamer bit 705. Thus, even at the start of the reaming, the foot 703 can brace the reamer tool 700 firmly against the bone or other tissue. The arrangement is also such that, subsequently, as the reaming proceeds by virtue of turning of the handle 701, the foot 703 is automatically drawn towards a proximal end of the lock nut 702, allowing the reamer bit 705 to project increasingly further from the foot 703, increasing the ream depth while the foot continues to brace the reamer tool 700 against the bone or other tissue. The foot 703 can continue moving towards the proximal end of the lock nut 702 until it abuts a shoulder 7023 of the lock nut 702, as illustrated in FIG. 10c, at which point the foot 703 provides a depth stop.

In alternative embodiments, in place of a screw bearing, the relative movement between the foot and the lock nut may be controlled through use of a spring mechanism or cam mechanism.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An electrode device that is removably implantable at least partially in a recess formed in bone, the electrode device comprising:
   a head configured to engage an outer surface of the bone; and
   a shaft connected to the head, the shaft configured to extend into the recess formed in the bone and comprising:
      a shaft body extending distally from the head in an axial direction of the shaft;
      a conductive element, the conductive element including a conductive surface at a distal end of the shaft; and
      a plurality of discrete anchor elements projecting from an outer surface of the shaft body in a transverse direction of the shaft,
   wherein a conductor extends through the head and is electrically connected to the conductive element,
   wherein an outer portion of the head is resiliently flexible and extends radially outwardly from the shaft body to a rim portion of the head, the rim portion having a distal-facing outer surface, the outer portion of the head curving distally as it extends towards the rim portion of the head such that the head has a concave distal facing outer surface between the shaft body and the rim portion and wherein the rim portion extends between the concave distal facing surface and an outer edge of the head, and
   wherein the plurality of discrete anchor elements projecting from the outer surface of the shaft body are configured to secure the shaft body in the recess upon press-fitting of the electrode device into the recess.

2. The electrode device of claim 1, wherein the anchor elements are configured to distort during removal of the electrode device from its implantation location.

3. The electrode device of claim 1, wherein the anchor elements are configured to remain intact during and after removal of the electrode device from the recess.

4. The electrode device of claim 1, wherein the shaft body is formed of a first material and the anchor elements are formed of a second material and wherein the second material is softer than the first material.

5. The electrode device of claim 1 having at least one of the following: the anchor elements integrally formed in one-piece with the shaft body; and the shaft body integrally formed in one-piece with all or part of the head.

6. The electrode device of claim 1, wherein the anchor elements are arranged in a staggered pattern on the outer surface of the shaft body.

7. The electrode device of claim 1, wherein at least one anchor element of the plurality of anchor elements is located, in the axial direction of the shaft, closer to the distal end of the shaft than one or more other anchor elements of the plurality of anchor elements.

8. The electrode device of claim 1, wherein a first pair of anchor elements of the plurality of anchor elements is located, in the axial direction of the shaft, at a first distance from the distal end of the shaft and a second pair of anchor elements of the plurality of anchor elements is located, in the axial direction of the shaft, at a second distance from the distal end of the shaft, the first and second distances being different.

9. The electrode device of claim 8, wherein the anchor elements of the first pair are located on opposite sides of the shaft body along a first transverse axis of the shaft and the anchor elements of the second pair are located on opposite sides of the shaft body along a second transverse axis of the shaft, the first and second transverse axes being orthogonal to each other.

10. The electrode device of claim 1, wherein the anchor elements each have a wedge shape that tapers in thickness towards the distal end of the shaft.

11. The electrode device of claim 10, wherein the wedge shape is defined by a rear surface that faces the head of the electrode device and a side surface that extends from an outer edge of the rear surface towards the distal end of the electrode device.

12. The electrode device of claim 11, having at least one of: the rear surface extending across a plane having an angle relative to a transverse plane of the electrode device that is greater or equal to 5°; and the side surface being curved.

13. The electrode device of claim 1, wherein the conductor is a conductive wire electrically connecting to a proximal end surface of the conductive element, the proximal end surface of the conductive element being located inside the head of the electrode device.

14. The electrode device of claim 13, wherein the conductive wire is welded or soldered to the proximal end surface and the proximal end surface comprises a recess configured to retain molten material during the welding or soldering.

15. The electrode device of claim 13, comprising a lead extending from the head, the conductive wire extending through the lead, the lead extending from the head at a strain relief portion of the head.

16. The electrode device of claim 15, wherein the strain relief portion is curved to match a curvature of a skull.

17. The electrode device of claim 15 wherein, across a transverse plane of the electrode device, the head, including the strain relief portion, has a tear-drop shape.

18. The electrode device of claim 1, wherein the head has a convex proximal facing surface.

19. The electrode device of claim 1, wherein the head acts as a spring to place tension on the anchor elements when the shaft is located in the recess.

* * * * *